United States Patent [19]
Gray et al.

[11] Patent Number: 6,040,307
[45] Date of Patent: Mar. 21, 2000

[54] METHODS AD COMPOSITIONS OF (−) KETOCONAZOLE FOR TREATING FUNGAL YEAST AND DERMATOPHYTE INFECTIONS

[75] Inventors: Nancy M. Gray, Marlborough, Mass.; Raymond Leon Woosley, Washington, D.C.

[73] Assignee: Sepracor Inc., Marlborough, Mass.

[21] Appl. No.: 09/314,229

[22] Filed: May 18, 1999

Related U.S. Application Data

[63] Continuation of application No. 08/906,129, Aug. 5, 1997, abandoned, which is a continuation of application No. 08/558,768, Nov. 15, 1995, abandoned, which is a continuation of application No. 08/281,858, Jul. 28, 1994, abandoned, which is a continuation of application No. 07/995,291, Dec. 22, 1992, abandoned.

[51] Int. Cl.$^7$ .......................... A61K 31/495; A61K 31/50
[52] U.S. Cl. ............................................ 514/252
[58] Field of Search .............................. 514/252

[56] References Cited

U.S. PATENT DOCUMENTS

| | | |
|---|---|---|
| 4,144,346 | 3/1979 | Heeres et al. . |
| 4,223,036 | 9/1980 | Heeres et al. . |
| 4,358,449 | 11/1982 | Heeres et al. . |

FOREIGN PATENT DOCUMENTS 0 396 184   11/1990   European Pat. Off. .

OTHER PUBLICATIONS

"Antimycotic Imidazoles. Part 4. Synthesis and Antifungal Activity of Ketoconazole, a New Potent Orally Active Broad–Spectrum Antifungal Agent," by j. Heeres, L.J.J. Backx, J.H. Mostmans and J. Van Cutsem; Journal of Medicinal Chemistry, vol. 22, No. 8, (1979), pp. 1003–1005.
"Hepatic reactions associated with ketoconazole in the United Kingdom," by G Lake–Bakaar, P.J. Scheuer and S. Sherlock; British Medical Journal, vol. 294, (1987), pp. 419–422.
"1–(1–Indanyl)– and 1–(1–Tetralyl)imidazole–5–carboxylate Esters, a Novel Type of Antifungal Agents," by E.F. Godefroi, J. Van Cutsem, C.A.M. Van Der Eycken and P.A.J. Janssen; Journal Medicinal Chemistry, vol. 10, (1967), pp. 1160–1161.
"Ketoconazole—a new broad spectrum orally active antimycotic[1]," by D. Thienpont, J. Van Cutsem, F. Van Gerven, J. Heeres ad P.A.J. Janssen; Experientia, vol. 35, (1979), pp. 606–607.
"Stereoisomers of Ketoconazole: Preparation and Biological Activity," by D.M. Rotstein, D.J. Kertesz, K.A.M. Walker and D.C. Swinney; Journal of Medicinal Chemistry, vol. 35, (1992), pp. 2818–2825.
J.E.F. Reynolds 'Matindale, The Extra Pharmacopoeia' 1989, The Pharmaceutical Press, London Press, London pp. 426—p. 429.
"cis–1–Acetyl–4–(4–{[2–(2, 4–dichlorophenyl)–2–(1H–1–imidazolylmethyl)–1, 3–dioxolan–4–yl]methoxy}phenyl)piperazine: Ketoconazole. A Crystal Structure with Disorder" by O.M. Peeters, N.M. Blaton and C.J. DeRanter; ACTA Crystallographica, vol. B35 (1979), pp. 2461–2464.
"In Vitro and In Vivo Effects of the Antimycotic Drug Ketoconazole on Sterol Synthesis" by Hugo Van Den Bossche, Gustaaf Willemsens, Willy Cools, Frans Cornelissen, William F. Lauwers, and Jan M. Van Cutsem; Antimicrobial Agents and Chemotherapy, vol. 17 Jun. (1980), pp. 922–928.
"Molecular Basis for the Antimycotic and Antibacterial Activity of N–Substituted Imidazoles and Triazoles: the Inhibition of Isoprenoid Biosynthesis", Vanden Bossche et al. *Pestic. Sci 15* , 188–198 (1984).

*Primary Examiner*—William R. A. Jarvis
*Attorney, Agent, or Firm*—Heslin & Rothenberg, P.C.

[57] ABSTRACT

Methods and compositions are disclosed utilizing the optically pure (−) isomer of ketoconazole. This compound is a potent drug for the treatment of local and systemic fungal, yeast, and dermatophyte infections, while avoiding the concomitant liability of adverse effects associated with the racemic mixture of ketoconazole.

8 Claims, No Drawings

METHODS AD COMPOSITIONS OF (−) KETOCONAZOLE FOR TREATING FUNGAL YEAST AND DERMATOPHYTE INFECTIONS

CROSS REFERENCE TO RELATED APPLICATIONS

This application is a continuation of application Ser. No. 08/906,129, filed Aug. 5, 1997, now abandoned, which is a continuation of application Ser. No. 08/558,768, filed Nov. 15, 1995, now abandoned, which is a continuation of application Ser. No. 08/281,858, filed Jul. 28, 1994, now abandoned, which was a continuation of application Ser. No. 07/995,291, filed Dec. 22, 1992, now abandoned.

BACKGROUND OF THE INVENTION

This invention relates to novel compositions of matter containing optically pure (−) ketoconazole. These compositions possess potent activity in treating local and systemic fungal, yeast and dermatophyte infections while avoiding adverse effects associated with the administration of the racemic mixture of ketoconazole. Adverse effects include, but are not limited to, hepatotoxicity, arrhythmia, hypersensitivity reactions, including urticaria, nausea, vomiting, abdominal pain, headache, dizziness, and elevations in serum liver enzymes. Also disclosed are methods for treating the foregoing infections in a human while avoiding the adverse effects that are associated with the racemic mixture of ketoconazole by administering the (−) isomer of ketoconazole to said human.

The active compound of these compositions and methods is an optical isomer of ketcoconazole, which is described by Heeres et al., *J. Med. Chem.* 22, (8), 1003–1005 (1979); Heel et al., *Drugs*, 23, 1–36, (1982) and in U.S. Pat. Nos. 4,144,346, 4,223,036 and 4,358,449. Chemically, the active compound is the (−) isomer of cis-1-acetyl-4-[4-[[2-(2,4-dichlorophenyl)-2-(1H-imidazole-1-ylmethyl)-1,3-dioxolan-4-yl]methoxy]phenyl]piperazine (I). This isomer will hereinafter be referred to as (−) ketoconazole.

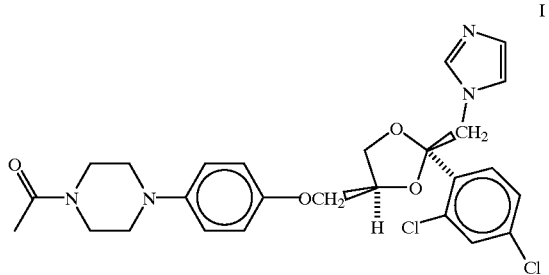

I 1-acetyl-4-[4-[[2-(2,4-dichlorophenyl)-2-(1H-imidazole-1-ylmethyl)-1,3-dioxolan-4-yl]methoxy]phenyl]piperazine has two centers of asymmetry and therefore exists as two enantiomeric pairs of diastereomers. Of these, the cis diastereomer is the most active as an antifungal agent. Ketoconazole is available commercially only as the racemic cis diastereomer, (R,S) plus (S,R) in a 1:1 ratio, and the generic name ketoconazole refers to this enantiomeric mixture. The racemic mixture of ketoconazole that is commercially available for administration is a free base, but the pharmacology of salts will be essentially similar.

The graphic representations of racemic, ambiscalemic and scalemic or enantiomerically pure compounds used herein are taken from Maehr *J. Chem. Ed.* 62, 114–120 (1985). Thus, solid and broken wedges are used to denote the absolute configuration of a chiral element; wedge outlines and dotted or broken lines (e.g. I) denote enantiomerically pure compounds of indeterminate absolute configuration.

Many organic compounds exist in optically active forms, i.e. they have the ability to rotate the plane of plane-polarized light. In describing an optically active compound, the prefixes D and L (commonly used only with sugars, amino acids and related compounds) or R and S (universally used) denote the absolute configuration of the molecule about its chiral center(s). The prefixes d and l or (−) and (−) are employed to designate the sign of rotation of plane-polarized light by the compound, with (−) or l meaning that the compound is levorotatory. A compound prefixed with (−) or d is dextrorotatory. There is no correlation between nomenclature for the absolute stereochemistry and for the rotation of an enantiomer. Thus, D-lactic acid is the same as (−) lactic acid, and L-lactic acid is (−). For a given chemical structure, these compounds, called stereoisomers, are identical except that they are mirror images of one another. A specific stereoisomer may also be referred to as an enantiomer, and a mixture of such isomers is often called an enantiomeric or racemic mixture.

Ketoconazole is an orally active, broad-spectrum antifungal agent. The compound, an imidazole derivative structurally related to miconazole and clotrimazole, impairs the synthesis of ergosterol, which is the principal sterol of fungal cell membranes. This presumably results in an increased permeability and leakage of intracellular content. At high concentration, cellular internal organelles involute, peroxisomes increase, and necrotic changes occur.

Following oral administration, ketoconazole provides, at lower doses, a linear increase in serum concentration. The compound is eventually metabolized to several inactive metabolites through oxidation and degradation of the imidazole and piperazine rings, dealkylation, and hydroxylation. While some of a given dose is excreted in the urine, the major route of excretion is via the bile into the intestinal tract [see Brass, C. et al., *Antimicro. Agents and Chemotherapy* 21, 151–158 (1982); *Physicians' Desk Reference* 46, 1144–1146 (1992) Medical Economics Co., Inc., Montvale, N.J.].

The racemic mixture of ketoconazole is presently used primarily as an antifungal agent for such systemic infections as candiduria, blastomycosis, coccidioidomycosis, histoplasmosis, chromomycosis, paracoccidioidomycosis, candidiasis, chronic mucocutaneous candidiasis, and oral thrush. The compound is also indicated for severe cutaneous dermatophyte infections in patients who have not responded to topical therapy or oral griseofulvin.

Systemic fungal diseases (systemic mycoses) are usually chronic, very slowly developing conditions induced by opportunistic causative fungi which may not normally be pathogenic. However when they enter a host compromised by HIV infection, ionizing irradiation, corticosteroids, immunosuppressives, etc. or by such conditions as emphysema, bronchiectasis, diabetes mellitus, leukemia, burns and the like, they may become pathogenic. Symptoms in such fungal diseases are generally not intense, and may include fever, chills, anorexia and weight loss, malaise, and depression. Fungal diseases are often confined to typical anatomic distributions, and many involve a primary focus in the lung, with more characteristic manifestations of specific fungal infections when the fungus disseminates from a primary focus. For example, coccidicidomycosis occurs in a primary form as an acute, benign, self-limiting respiratory disease, with progressive disease developing from the primary form as a chronic, often fatal infection of the skin, lymph glands, spleen and liver. Similarly, blastomycosis primarily involves the lungs, and occasionally spreads to the skin. Other infectious diseases such as paracoccidioidomycosis and candidiasis offer a different course, and depending on the etiology may exhibit several forms involving the skin, mucous membranes, lymph nodes, and internal organs. The diagnosis of specific fungal diseases may be made by isolation of the causative fungus from sputum, urine, blood, or the bone marrow, or with prevalent fungus types by evidence of tissue invasion.

Superficial fungal infections are caused by dermatophytes or fungi that involve the outer layers of the skin, hair or nails. The infections may result in a mild inflammation, and cause intermittent remissions and exacerbations of a gradually extending, scaling, raised lesion. Yeast infections including candidiasis, and oral candidiasis (thrush) are usually restricted to the skin, and mucous membranes, and the symptoms vary with the site of infection. Commonly, infections appear as erythematous, often itchy, exudative patches in the axillas, umbilicus, groin, between toes, and on fingerwebs. Oral thrush involves an inflamed tongue, or buccal mucosa and presents as white patches of exudate, while chronic mucocutaneous candidiasis is characterized by red, pustular, crusted, thickened lesions on the forehead or nose.

Many of the imidazole antifungal agents, including ketoconazole, share the same adverse effects. These adverse effects include, but are not limited to, nausea, vomiting, anemia, thrombocytosis, hypersensitivity reactions, hepatotoxicity and some central nervous system toxicity. The racemic mixture of ketoconazole has been found to cause nausea and vomiting, anorexia, headache, and dizziness. Hypersensitivity reactions including urticaria, abdominal pain, and hepatotoxicity and elevations in serum liver enzymes are also associated with the administration of the drug. The most common side effects are gastrointestinal, and they occur in 5 to 10% of patients. Hepatoxicity is less common but more serious. Indeed, the use of oral ketoconazole as a first line antifungal is discouraged because of the potentially serious consequences of the low incidence of hepatotoxicity [See, for example, Schaffner *Schweiz Med. Wochenschr.* 121, 1413–1418 (1991)]. A review article in the British Medical Journal [Lake-Bakaar et al. *Brit. Med. J.* 294, 419–422 (1987)] reviewed 82 reports, including 5 deaths, of hepatotoxicity associated with ketoconazole therapy during 1981–1984 in the United Kingdom. An analysis of the 75 cases that had been adequately followed up suggested that 16, including 3 deaths, were probably related to treatment with the drug. Of the remainder, 48 were possibly related to treatment. Hepatoxicity appeared more common in women. The results of serum liver function tests suggested hepatocellular injury in 10 of the 16 probably related cases; the rest showed a mixed pattern. The results of histological examination of the liver often showed evidence of cholestasis. Allergic manifestations such as rash and eosinophilia were rare. Hepatitis was usually reversible when treatment was stopped, with the results of liver function tests returning to normal after an average of 3.1 months. It was concluded that clinical and biochemical monitoring at regular intervals for evidence of hepatitis was advised during long term treatment with racemic ketoconazole to prevent possible serious hepatic injury.

In addition we have found evidence in our own studies in isolated guinea pig hearts that the administration of racemic ketoconazole may be associated with an increased risk of cardiac arrhythmia. Arrhythmia has not been heretofore reported as a side effect of systemic racemic ketoconazole, although a particular subtype of arrhythmia, torsades de pointes, has been reported when racemic ketoconazole was administered concurrently with terfenadine. The lack of clinical reports of arrhythmia or QT anomalies may simply be a reflection of the fact that oral racemic ketoconazole is only indicated as a later resort when other preferred therapies have failed, and thus there is a relatively small subject population.

Thus it would be particularly desirable to find a compound with the advantages of the racemic mixture of ketoconazole which would not have the aforementioned disadvantages.

SUMMARY OF THE INVENTION

It has now been discovered that the optically pure (−) isomer of ketoconazole is an effective agent for treating local and systemic fungal, yeast, and dermatophyte infections that avoids adverse effects associated with the administration of the racemic mixture, including but not limited to hepatotoxicity, arrhythmogenicity, dizziness, elevations in serum liver enzymes, hypersensitivity reactions, urticaria, headache, nausea, vomiting and abdominal pain. The present invention also includes methods for treating local and systemic fungal, yeast and dermatophyte infections in a human while avoiding the adverse effects that are associated with the racemic mixture of ketoconazole, by administering the optically pure (−) isomer of ketoconazole to said human.

DETAILED DESCRIPTION OF THE INVENTION

The present invention encompasses a method of treating local and systemic fungal, yeast and dermatophyte infections in a human, which comprises administering to a human in need of such antiinfective therapy, an amount of (−) ketoconazole, or a pharmaceutically acceptable salt thereof, substantially free of its (+) stereoisomer, said amount being sufficient to alleviate such infections. The method avoids the concomitant liability of adverse effects associated with the administration of racemic ketoconazole by providing an amount of (−) ketoconazole which is insufficient to cause the adverse effects associated with the racemic mixture of ketoconazole.

The present invention also encompasses an antiinfective composition for the treatment of a human in need of therapy for systemic or topical fungal, yeast or dermatophyte infection, which comprises an amount of (−) ketoconazole, or a pharmaceutically acceptable salt thereof, substantially free of its (+) stereoisomer, said amount being sufficient to alleviate said infection. The composition should provide a doses which is insufficient to cause the adverse effects associated with racemic ketoconazole.

The available racemic mixture of ketoconazole (i.e. a 1:1 racemic mixture of the two enantiomers of the cis diastereomer) possesses antiinfective activity and provides therapy against many fungi, yeasts and dermatophytes; however, this racemic mixture, while offering the expectation of efficacy, causes adverse effects. Utilizing the substantially optically pure or optically pure isomer of ketoconazole results in clearer dose related definitions of efficacy, diminished adverse effects, and accordingly, an improved therapeutic index. It is therefore more desirable to administer the (−) isomer of ketoconazole than racemic ketoconazole.

The term "adverse effects" includes, but is not limited to, arrhythmogenicity, hepatotoxicity and elevations in serum liver enzymes, hypersensitivity reactions including urticaria, nausea, vomiting, abdominal pain, headache, dizziness and the like.

The term "substantially free of its (+) stereoisomer" as used herein means that the compositions contain a greater proportion of the (−) isomer of ketoconazole in relation to the (+) isomer. In a preferred embodiment, the term "substantially free of its (+) isomer" as used herein means that the composition is at least 90% by weight of (−) ketoconazole and 10% by weight or less of (+) ketoconazole. In a more preferred embodiment the term "substantially free of the (+) stereoisomer" means that the composition contains at least 99% by weight of (−) ketoconazole, and 1% or less of (+) ketoconazole. In the most preferred embodiment, the term "substantially free of its (+) stereoisomer" as used herein means that the composition contains greater than 99% by weight of (−) ketoconazole. These percentages are based upon the total amount of ketoconazole in the composition. The terms "substantially optically pure (−) isomer of ketoconazole" or "substantially optically pure (−) ketoconazole" and "optically pure (−) isomer of ketoconazole" and "optically pure (−) ketoconazole" are also encompassed by the above-described amounts.

The chemical synthesis of the racemic mixture of ketoconazole can be performed by the method described in Heeres, J. et al., *J. Med. Chem*,. 22, 1003–1005 (1979) and in U.S. Pat. Nos. 4,144,346 and 4,223,036. Individual isomers of ketoconazole may be obtained by resolution of the racemic mixture of enantiomers using conventional means. The ketoconazole may be resolved with an optically active acid such as tartaric acid at the imidazo-dioxolane alcohol or ester state or at the final product. Other standard methods of resolution known to those skilled in the art, including but not limited to simple crystallization and chromatographic resolution, can be used. [See for example, Stereochemistry of Carbon Compounds, E. L. Eliel, McGraw Hill (1962); "Tables of Resolving Agents" Wilen and Lochmuller, *J. Chromatography* 113, 283–302 (1975).] Additionally, the optically pure (−) isomer can be prepared from the racemic mixture by enzymatic biocatalytic resolution. See for example, U.S. Pat. Nos. 5,057,427 and 5,077,217, the disclosures of which are incorporated herein by reference. Thus an ester of the 2-(imidazolylmethyl)dioxolane-4-acetic acid intermediate can be enzymatically resolved.

The four possible stereoisomers of ketoconazole have recently been prepared by stereocontrolled synthesis from optically active dioxolane precursor [Rotstein et al. *J. Med. Chem.* 35, 2818–2825 (1992)]. The (−) isomer of cis ketoconazole, which is the subject of the present invention, appears to be of the (2S,4R) configuration. When tested against mammalian enzymes involved in steroic metabolism, the two enantiomers were found to have varying relative potencies as inhibitors depending on the particular enzyme. The authors concluded that, for hormone dependent prostate cancer, there was no apparent advantage to the use of the enantiomerically pure cis compound. That the (−) isomer would enjoy a specific advantage in the treatment of fungal infections may therefore be somewhat surprising.

The magnitude of a prophylactic or therapeutic dose of (−) ketoconazole in the acute or chronic management of disease will vary with the severity of the condition to be treated, and the route of administration. The dose, and perhaps the dose frequency, will also vary according to the age, body weight, and response of the individual patient. In general, the total daily dose range, for (−) ketoconazole, for the conditions described herein, is from about 50 mg to about 1200 mg, in single or divided doses. Preferably, a daily dose range should be between about 100 mg to about 1000 mg, in single or divided doses, while most preferably, a daily dose range should be between about 200 mg to about 600 mg, in single or divided doses. In managing the patient, the therapy should be initiated at a lower dose, perhaps about 100 mg to about 300 mg, and increased up to about 600 mg or higher depending on the patient's global response. It is further recommended that children, and patients over 65 years, and those with impaired renal, or hepatic function, initially receive low doses, and that they be titrated based on individual response(s) and blood level(s). It may be necessary to use dosages outside these ranges in some cases as will be apparent to those skilled in the art. Further, it is noted that the clinician or treating physician will know how and when to interrupt, adjust, or terminate therapy in conjunction with individual patient response. The term "an amount sufficient to alleviate such infections but insufficient to cause said adverse effects" is encompassed by the above-described dosage amounts and dose frequency schedule.

Any suitable route of administration may be employed for providing the patient with an effective dosage of (−) ketoconazole. For example, oral, rectal, parenteral (subcutaneous, intramuscular, intravenous), transdermal, topical and like forms of administration may be employed. Dosage forms include tablets, troches, dispersions, suspensions, solutions, capsules, patches, ointments, creams, shampoos and the like.

The pharmaceutical compositions of the present invention comprise (−) ketoconazole as the active ingredient, or a pharmaceutically acceptable salt thereof, and may also contain a pharmaceutically acceptable carrier, and optionally, other therapeutic ingredients.

The terms "pharmaceutically acceptable salts" or "a pharmaceutically acceptable salt thereof" refer to salts prepared from pharmaceutically acceptable non-toxic acids or bases including inorganic acids and bases and organic acids and bases. Since the compound of the present invention is basic, salts may be prepared from pharmaceutically acceptable non-toxic acids including inorganic and organic acids. Suitable pharmaceutically acceptable acid addition salts for the compound of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic (mesylate), mucic, nitric, pamoic, pantothenic, phosphoric, succinic, sulfuric, tartaric, p-toluenesulfonic, and the like.

The compositions of the present invention include compositions such as suspensions, solutions, elixirs, aerosols, and solid dosage forms. Carriers such as starches, sugars, microcrystalline cellulose, diluents, granulating agents, lubricants, binders, disintegrating agents, and the like, are commonly used in the case of oral solid preparations (such as powders, capsules, and tablets), with the oral solid preparations being preferred over the oral liquid preparations. The most preferred oral solid preparation is tablets.

Because of their ease of administration, tablets and capsules represent the most advantageous oral dosage unit form, in which case solid pharmaceutical carriers are employed. If desired, tablets may be coated by standard aqueous or nonaqueous techniques.

A second preferred route of administration is topically, for which creams, ointments, shampoos, and the like are well suited.

In addition to the common dosage forms set out above, the compounds of the present invention may also be administered by controlled release means and/or delivery devices such as those described in U.S. Pat. Nos.: 3,845,770; 3,916, 899; 3,536,809; 3,598,123; and 4,008,719; the disclosures of which are hereby incorporated by reference.

Pharmaceutical compositions of the present invention suitable for oral administration may be presented as discrete units such as capsules, cachets, or tablets, or aerosol sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 100 mg to about 300 mg of the active ingredient. Most preferably, the tablet, cachet or capsule contains either one of three dosages, about 50 mg, about 100 mg, or about 200 mg of the active ingredient.

For topical application, there are employed as non-sprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g., preservatives, stabilizers, wetting agents, buffers or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon.

The invention is further defined by reference to the following examples describing in detail the preparation of the compositions of the present invention as well as their utility. It will be apparent to those skilled in the art that many modifications, both to materials and methods may be practiced without departing from the purpose and interest of this invention.

Microbiological and pharmacologic studies can be used to determine the relative potency and the profile of specificity of the optically pure enantiomers, and the racemic mixture of ketoconazole as antimycotic agents with a broad spectrum of activity against many fungi, yeast, and dermatophytes.

With respect to antimicrobial activity of the aforementioned compounds, selected experiments are illustrated to profile useful antimicrobial activity, and not to limit this invention in any way, including the scope of susceptible microorganisms. Antifungal imidazoles may be evaluated in vitro at several concentrations (in $\mu$g/ml) against a number of fungi and bacteria. (see Godefroi et al., *J. Med. Chem.* 10, 1160, 1967; Heeres, J. et al., *J. Med. Chem.* 22, (8), 1003–1005, 1979 and U.S. Pat. No. 4,144,346). The fungistatic assay is carried out in Sabouraud's liquid (1 g of neopeptone Difco and 2 g of glucose Difco per 100 mL of distilled water) in 16×160 mm test tubes, each containing 4.5 mL of liquid medium which has been autoclaved at 120° for 5 min. The compounds to be tested are dissolved in 50% alcohol at initial concentration of 20 mg/mL. The solutions are subsequently diluted with sterile distilled water to give a concentration of 10 mg/mL. Successive decimal dilutions are made in distilled water. To tubes containing 4.5 mL of Sabouraud's liquid medium 0.5 mL of the solution of the drug is added, thereby obtaining concentrations of 1000, 500, 100, 10, and 1 $\mu$g/mL of medium. Control tubes are prepared by adding 0.5 mL of distilled water to 4.5 of mL medium, alcohol being added to give concentrations identical with the tubes containing 1000 and 500 $\mu$g of the drug. The filamentous fungi are incubated in Sabouraud's agar at 25° for 2–3 weeks. A block of 2×2×2 mm is then inoculated into the medium. All cultures are made in duplicate and are incubated at 25° for 14 days. Ketoconazole antifungal activity is enhanced in vitro in Sabouraud broth containing 10% inactivated bovine serum, and depends on the test medium used. Complete or marked inhibition of growth in Sabouraud broth after 14 days of incubation may be observed with microsporum canis, trichophyton mentagrophytes, candida tropicalis, candida albicans, and other fungi and bacteria. Concentration/response curves may be compared for ketoconazole, its isomers, and such standard agents as miconazole, as regards scope, and potency.

In vivo activity of ketoconazole and the optically pure enantiomers may be compared against experimental cutaneous candidosis in guinea pigs, and vaginal candidosis in rats. The in vivo activity of the compounds in vaginal candidosis is evaluated by inducing vaginal infection with C. albicans in ovariectomized and hysterectomized Wistar rats (100 g) which are treated weekly with 100 $\mu$g of estradiol undecanoate in sesame oil, subcutaneously. Animals in pseudooestrus are infected intravaginally with a fixed concentration of C. albicans in saline. Control of infection or cure is estimated by taking vaginal smears at fixed days after infection. Drugs to be evaluated, and compared on a mg/kg basis, may be given prophylactically, or therapeutically and their efficacy judged by comparison the ratio of negative animals to the total number in each drug group. In similar studies, the activity against cutaneous candidosis in guinea pigs (Van Cutsem, J. et al. *Chemotherapy* 17, 392, 1972) provides the basis of comparison between the racemate and enantiomers of ketoconazole.

The potential for promoting arrhythmia is evaluated by examining the effects of the optically pure isomers of ketoconazole on cardiac action potential and contractility in human and canine hearts.

Torsades de pointes is a well known side effect of anti-arrhythmic drugs, such as quinidine, sotalol and acetyl-procainamide, which cause a prolongation of cardiac repolarization. All of these drugs have in common the ability to block a cellular potassium channel called the delayed rectifier ($I_k$), and it is generally assumed that this is mechanistically linked to their ability to induce the syndrome of torsades de pointes. [See Zehender et al. *Cardiovascular Drugs Ther.*, 5 515–530 (1991).]

We have found evidence in our own studies that racemic ketoconazole increases QT duration and action potential duration in isolated guinea pig hearts. The hearts were perfused with an oxygenated Tyrode's solution, containing 0.0; 1.0; 5.0 or 10.0 $\mu$M of ketoconazole. QT duration and action potential duration (APD) were measured from cardiac electrodes. APD was measured at 50% (APD-50) and 90%

(APD-90). In the table, "N" is the number of hearts, and QT and APD are measured in milliseconds.

| | N | Drug Conc. ($\mu M$) | QT | APD-90 | APD-50 |
|---|---|---|---|---|---|
| Baseline | 2 | — | 230 ± 10 | 185 ± 10 | 145 ± 5 |
| Ketoconazole | 2 | 1.0 | 232 ± 9 | 195 ± 5 | 149 ± 1 |
| Baseline | 3 | — | 233 ± 9 | 187 ± 9 | 147 ± 5 |
| Ketoconazole | 3 | 5.0 | 261 ± 8 | 221 ± 8 | 163 ± 5 |
| Baseline | 3 | — | 237 ± 12 | 177 ± 14 | 140 ± 8 |
| Ketoconazole | 3 | 10.0 | 178 ± 31 | 233 ± 9 | 173 ± 2 |

According to the studies of Zehender et al., these results are indicative of a potential arrhythmogenic effect of racemic ketoconazole in vivo.

To confirm this observation in human tissue in vitro, healthy right ventricular trabeculae are harvested from failing human hearts removed at the time of transplantation and are placed in tissue baths, designed for microelectrode impalement. Following an equilibration period, a thin trabeculum is impaled intracellularly, and the action potential is recorded. After equilibration, the test compounds at doses of $10^{-8}$ and $10^{-4}$ M are added in cumulative fashion. Action potential duration is measured at 50% (APD-50) and/or 90% (APD-90) repolarization. In separate experiments, trabeculae are divided into 3 subgroups receiving either the (−) enantiomer, (+) enantiomer, or racemate to determine the respective effects on contractility.

To confirm the observation in vivo, mongrel dogs of either sex weighing 5–20 kg are anesthetized and instrumented by standard techniques for blood pressure and EKG. A solid state transducer for dP/dT is placed in the left cardiac ventricle, and an epicardial electrode is put into place. The test compound is infused at progressively higher doses, beginning at 1 $\mu$g/kg/min for 15 minutes and increased incrementally until a cardiovascular collapse ensues. Parameters measured are: blood pressure, heart rate, dP/dT, and the QT-interval. Measurements of hemodynamics and electrical activity are made in response to the (−) enantiomer, (+) enantiomer and racemate.

The potential for promoting hepatotoxicity is assessed in vitro in human hepatic microsomes and human lymphocytes. Hepatic microsomes are prepared from human liver. Tissue is thawed and then homogenized in 0.15 M KCl in a Polytron homogenizer. The homogenate is centrifuged and the pellet is resuspended and homogenized in 0.15 M KCl. Aliquots are frozen and stored at −70° C. Humen lymphocytes are aseptically isolated from fresh, heparinized human blood. Blood is diluted with Eagle's minimal essential medium and layered on Ficoll-Paque. The samples are centrifuged, and lymphocytes are then removed from the aqueous-Ficoll interface and suspended in medium (15 Mm HEPES, pH 7 4). The cells are then centrifuged, washed once in the HEPES medium, and resuspended.

Cytotoxicity is assessed by the Conversion of 3-(4,5 dimethylthiazol-2-yl)-2,5-diphenyltetrazolium bromide (MTT) to a purple formazan. The conversion of MTT to dye is done in multiwell plates. After preparation, hepatic microsomes or lymphocytes are incubated alone or with the test compound in a concentration range from 1 to 400 $\mu$M at 37° C. in a humidified incubator. After incubation, the microsomes/cells are washed with 5% albumin in HEPES-buffered medium and resuspended. The microsomes/cells are then incubated at. 37° C. in a humidified incubator. After the incubation, 125 $\mu$g of MTT is added to each well. The plates are incubated at 37° C. and centrifuged. After centrifugation, 100 $\mu$L of isopropanol is added and, after incubation, the optical density is determined using an automated plate-reader.

EXAMPLE 1

Oral Formulation
Capsules

| | Quantity per capsule in mg | | |
|---|---|---|---|
| Formula | A | B | C |
| (−) Ketoconazole | 50 | 100 | 200 |
| Lactose | 380 | 330 | 230 |
| Cornstarch | 65 | 65 | 65 |
| Magnesium Stearate | 5 | 5 | 5 |
| Compression Weight | 500 | 500 | 500 |

The active ingredient, (−) ketoconazole, is sieved and blended with the excipients. The mixture is filled into suitably sized two-piece hard gelatin capsules using suitable machinery. Other doses may be prepared by altering the fill weight and if necessary, changing the capsule size to suit.

EXAMPLE 2

Oral Formulation
Tablets

| | Quantity per tablet in mg | | |
|---|---|---|---|
| Formula | A | B | C |
| (−) Ketoconazole | 50 | 100 | 200 |
| Lactose | 109 | 309 | 209 |
| Cornstarch | 30 | 30 | 30 |
| Water | 300 | 300 | 300 |
| (per thousand Tablets)* | mL | mL | mL |
| Cornstarch | 60 | 60 | 60 |
| Magnesium Stearate | 1 | 1 | 1 |
| Compression Weight | 250 | 500 | 500 |

The active ingredient is blended with the lactose until a uniform blend is formed. The smaller quantity of cornstarch is blended with the water to form the resulting cornstarch paste. This is then mixed with the uniform blend until a uniform wet mass is formed and the remaining cornstarch is added and mixed until uniform granules are obtained. The granules are screened through a suitable milling machine using a ¼" stainless steel screen. The milled granules are dried in a suitable drying oven and milled through a suitable milling machine again. The magnesium stearate is then blended and the resulting mixture is compressed into tablets of desired shape, thickness, hardness and disintegration.

What is claimed is:

1. A method for treating local and systemic fungal, yeast and dermatophyte infections in a human which comprises administering to the human, in need of antiinfective therapy, an amount of (−) ketoconazole, or a pharmaceutically acceptable salt thereof, substantially free of its (+) stereoisomer, said amount being sufficient to alleviate said infections.

2. A method for treating local and systemic fungal, yeast and dermatophyte infections in a human while avoiding the concomitant liability of adverse effects associated with racemic ketoconazole, which comprises administering to the human, in need of antiinfective therapy, an amount of (−) ketoconazole, or a pharmaceutically acceptable salt thereof, substantially free of its (+) stereoisomer, said amount being sufficient to alleviate said infection but insufficient to cause said adverse effects.

3. The method of claim 2 wherein (−) ketoconazole is administered by intravenous infusion, transdermal delivery, or orally as a tablet or a capsule.

4. The method of claim 3 wherein the amount of (−) ketoconazole or a pharmaceutically acceptable salt thereof administered is from about 50 mg to about 1200 mg per day.

5. The method of claim 4 wherein the amount administered is from about 100 mg to about 1000 mg per day.

6. The method of claim 5 wherein the amount administered is from about 200 mg to about 600 mg per day.

7. The method of claim 1 wherein the amount of (−) ketoconazole or a pharmaceutically acceptable salt thereof is greater than approximately 90% by weight of the total weight of ketoconazole.

8. The method of claim 1 wherein the amount of said (−) ketoconazole or a pharmaceutically acceptable salt thereof, substantially free of its (+) stereoisomer, is administered together with a pharmaceutically acceptable carrier.

* * * * *

UNITED STATES PATENT AND TRADEMARK OFFICE
CERTIFICATE OF CORRECTION

PATENT NO.    : 6,040,307
DATED         : March 21, 2000
INVENTOR(S)   : Gray et al.

It is certified that error appears in the above-identified patent and that said Letters Patent is hereby corrected as shown below:

On the title page:

Item [54], line 1, delete "AD" and replace with --AND--.

Col. 1, line 1, delete "AD" and replace with --AND--.

Signed and Sealed this

Sixth Day of February, 2001

*Attest:*

Q. TODD DICKINSON

*Attesting Officer*      *Director of Patents and Trademarks*